(12) United States Patent
Glencross

(10) Patent No.: US 7,892,551 B2
(45) Date of Patent: Feb. 22, 2011

(54) ANTIBODY KIT FOR ENUMERATION OF CD4+ LYMPHOCYTES

(75) Inventor: Deborah Kim Glencross, Houghton (ZA)

(73) Assignee: National Health Laboratory Service, Braamfrontein (ZA)

( * ) Notice: Subject to any disclaimer, the term of this patent is extended or adjusted under 35 U.S.C. 154(b) by 717 days.

(21) Appl. No.: 11/822,853

(22) Filed: Jul. 10, 2007

(65) Prior Publication Data

US 2007/0275413 A1 Nov. 29, 2007

Related U.S. Application Data

(60) Division of application No. 10/754,711, filed on Jan. 12, 2004, now Pat. No. 7,670,793, which is a continuation of application No. PCT/IB02/02725, filed on Jul. 11, 2002.

(30) Foreign Application Priority Data

Jul. 11, 2001 (ZA) .................................. 2001/5700

(51) Int. Cl.
*A61K 39/395* (2006.01)
(52) U.S. Cl. .............. 424/154.1; 424/130.1; 424/141.1; 424/142.1; 424/144.1; 424/152.1
(58) Field of Classification Search ........................ None
See application file for complete search history.

(56) References Cited

U.S. PATENT DOCUMENTS

| | | | |
|---|---|---|---|
| 3,896,307 | A | 7/1975 | Trowe |
| 5,064,616 | A | 11/1991 | Brosnan et al. |
| 5,385,822 | A | 1/1995 | Melnicoff et al. |
| 5,776,709 | A | 7/1998 | Jackson et al. |
| 5,812,419 | A | 9/1998 | Chupp et al. |
| 5,945,293 | A | 8/1999 | Siiman et al. |
| 6,010,902 | A * | 1/2000 | Ledbetter et al. ............ 435/328 |
| 2003/0018438 | A1 | 1/2003 | Nestor, Jr. et al. |

FOREIGN PATENT DOCUMENTS

EP 0470810 2/1992

OTHER PUBLICATIONS

Ian Storie et al., "Flow Rate Calibration II: A Clinical Evaluation Study Using PanLeucoGating as a Single-Platform Protocol", Clinical Cytometry, 55B:8-13 (2003).
D.K. Glencross et al., "Results from the WHO/NHLS/QASI CD4 Regional External Quality Assessment Scheme (REQAS): Multi-Site Evaluation of CD4 Technology Performance", 2nd South African AIDS Meeting, Jun. 2005.
W. Stevens et al., "Affordable HIV Diagnosis and Monitoring for Scaling Up ARV Treatment Programmes", The Southern African Journal of HIV Medicine, Sep. 2005, pp. 38-41.
L. Scott et al., "Monitoring Reproducibility of Single Analysis, Single Platform CD4 Cell Counts in a High Volume, Low Resource Laboratory Setting Using Sequential Bead Count Rates", Clinical Cytometry, 67B:31-32 (2005).
T. Rehle et al., "HIV-positive educators in South African public schools", Education Labour Relations Council, 2005.
T. Rehle et al., "Appendix and Addenda—HIV-positive educators in South African public schools", Education Labour Relations Council, 2005.
NCCLS, "Clinical Applications of Flow Cytometry: Quality Assurance and Immunophenotyping of Lymphocytes; Approved Guideline", 1998, Abstract, vol. 18, No. 21, pp. H-42 A.
U.S. Food and Drug Administration, "Recognized Consensus Standards", www.accessdata.fda.gov/scripts/cdrh/cfdocs/cfstandards/detail.CFM?Standard_identification_NO-10448, Mar. 30, 2006.
G. Vercauteren et al., "Impact of Who External Quality Assessment (EQA) programme on the laboratory performance of CD4 enumeration for monitoring of ARV therapy in Resource Limited settings", World Health Organization, Conference: AIDS2006 (Abstract), (2006).
D. Glencross et al., "Improved between-laboratory performance of South African NHLS laboratories using PLG CD4 methodology for the national antiretroviral (ARV) treatment programme", University of the Witwatersrand, Aug. 14, 2006 (Abstract).
D. Glencross et al., "CD45-Assisted PanLeucogating for Accurate, Cost-Effecive Dual-Platform CD4+ T-Cell Enumeration", Cytometry (Clinical Cytometry) 50: 69-77 (2002).
M. Willja et al., "Less Expensive CD4+ T Cell Monitorying Using Panleucogating", AIDS 2002 Barcelona, Jul. 7-12, 2002 (Abstract).
K. Pattanapanyasat et al., "A Multicenter Evaluation of the PanLeucogating Method and the Use of Generic Monoclonal Antibody Reagents for CD4 Enumeration in HIV-Infected Patients in Thailand", Cytometry Part B (Clinical Cytometry) 65B: 29-36 (2005).
K. Pattanapanyasat et al., "Low-Cost CD4 Enumeration in HIV-Infected Patients in Thailand", Asian Pacific Journal of Allergy and Immunology, 21: 105-113 (2003).
T. Denny et al., "Determination of CD4 and CD8 Lymphocyte Subsets by a New Alternative Fluorescence Immunoassay", Clinical and Diagnostic Laboratory Immunology, May 1995, p. 330-336.

(Continued)

*Primary Examiner*—Allison M Ford
(74) *Attorney, Agent, or Firm*—Buchanan, Ingersoll & Rooney PC

(57) ABSTRACT

The invention provides a method of enumerating the number of cells of a cell type in a cell sample by (a) counting the white blood cells in the cell sample to obtain the white blood cell population of the sample; (b) determining the proportion or percentage of the cells of the cell type in the white blood cell population in the sample; and (c) calculating the number of cells of the cell type in the sample. The cell type may be a lymphocyte sub-set selected from the group comprising CD4+ lymphocytes, CD 45 cells, CD19 cells, CD16 and CD56 positive cells, CD8 cells, CD3 cells or any combination thereof. The method is particularly useful in monitoring the immune status of a patient infected with HIV or other immune deficiency state or disease or condition where CD4+ lymphocytes or CD4+ T cells are monitored or counted. The invention also provides a kit comprising antibodies necessary for carrying out said cell enumeration.

3 Claims, 4 Drawing Sheets

OTHER PUBLICATIONS

L. Scott et al., "Antiviral Therapy 8 (suppl 1) Abstract No. 1226", $2^{nd}$ International AIDS Conference on HIV Pathogenesis and Treatment, France, 2003.

T. Denny et al., "A Multi-Lab Study of CD4 Counts Using Flow Cytometric PanLeukoGating (PLG): A Niaid-Daids Immunology Quality Assessment Program Study", $13^{th}$ Conference Retrovirology and Opportunistic Infection (CROI), Boston, Feb. 2006.

N. Sippy et al., "Comparison of the Panleucogating technique with four-color heterogenous gating for CD4+ T cell enumeration by flowcytometry in HIV-1 infected individuals in Barbados", Ladymeade Reference Unit, Ministry of Health, Barbados, No Date.

Centers for Disease Control (USA), "1997 revised guidelines for performing CD4+ T-cell determinations in persons infected with human immunodeficiency virus (HIV)", Morbidity and Mortality Weekly Report, vol. 46, No. RR-2, pp. I-II, 1-29, (1997).

Brando et al., "Cytofluorometric Methods for Assessing Absolute Numbers of Cell Subsets in Blood", Cytometry, 2000, vol. 42, pp. 327-346.

Nicholson et al., "Use of CD45 Fluorescence and Side-Scatter Characteristics for Gating Lymphocytes When Using the Whole Blood Lysis Procedure of Flow Cytometry", Cytometry, 1995, vol. 26, No. 1, pp. 16-21.

Schnizlein-Bick et al., "Evaluation of TruCount Absolute-Count Tubes for Determining CD4 and CD8 Cell Nos. in Human Immunodeficiency Virus-Positive Adults", Clinical and Diagnostic Laboratory Immunology, May 2000, vol. 7, No. 3, pp. 336-343.

Loken et al., "Establishing Optimal Lymphocyte Gates for Immunophenotyping by Flow Cytometry", 1990, vol. 11, pp. 453-459.

Barnett et al., "Absolute CD4+ T-Lymphocyte and CD34+ Stem Cell Counts by Single-Platform Flow Cytometry: The Way Forward", British Journal of Haematology, 1999, vol. 106, No. 4, pp. 1059-1062.

Sherman et al., "CD4T Cell Enumeration in HIV Infection with Limited Resources", Journal of Immunological Methods, 1999, vol. 222, No. 1-2, pp. 209-217.

Center et al., "The Lymphocyte Chemoattractant Factor", J. Lab Clin Med, 1995, vol. 125, No. 2, pp. 167-172.

Stewart et al., "Human T Lymphocytes and Monocytes Bear the Same LEU-3(T4) Antigen", Journal of Immunology, 1986, vol. 136, No. 10, pp. 3773-3778.

Dorland's Medical Dictionary, "Count- Counter" hhtp://merckmedicus.com/pplus/hcp/thcp_dorlands-content.jsp:48 pg=/ppdocs/us/common/dorlands/dorland/dmd-c-062.htm#961741 accessed Jun. 16, 2005.

* cited by examiner or

ANTIBODY KIT FOR ENUMERATION OF CD4+ LYMPHOCYTES

CROSS-REFERENCE TO RELATED APPLICATIONS

This application is a divisional of U.S. application Ser. No. 10/754,711, filed Jan. 12, 2004, pending, which is a continuation of PCT/IB02/02725 filed on Jul. 11, 2002, which claims priority from South Africa Patent Application No. 2001/5700 filed on Jul. 11, 2001, the entire content of which are hereby incorporated by reference.

BACKGROUND OF THE INVENTION

This invention relates to the enumeration of cells in a cell sample, for example in a bone marrow cell sample, a body fluid sample, a disaggregated tissue sample, a tissue fine needle aspiration sample or, in particular, a blood sample. More particularly, the invention relates to a method suitable for, but not limited to, enumerating the number of CD4+ lymphocytes in a blood sample.

There are several methods for performing cell counting which are currently available. The most popular method is flow cytometric cell testing. Non-flow cytometric methods are also available, although these methods are less widely used.

Flow Cytometric CD4+ T Cell Testing

Two methods of flow cytometric CD4 testing are utilized worldwide for CD4+ T cell enumeration. The first method involves the use of two machines and is referred to as the dual or double platform method (DP) (1). This method involves the use of specific panels of antibodies including CD3, CD4, CD8, CD19, CD16, CD56, and CD45. Various fluorochrome combinations can be used to form either two, three or four color combinations of antibody to constitute the various panels. Duplication of at least one measurement to ensure reproducibility e.g. CD3, is typically performed. In some instances it is recommended that CD14 expression is also used in the panel to exclude CD14 positive monocytes from the "lymphocyte" gate and ensure purity of the lymphocyte population studied.

The dual platform method makes use of a hematology analyzer to obtain an absolute lymphocyte count (ALC) [which is obtained by multiplication of two independently measured parameters viz. the white cell count and the % lymphocytes of the total white blood cell differential]. A flow cytometer is used to obtain a corresponding CD4 percentage (CD4%) of lymphocytes.

The CD4 antigen expressed on the surface of T cells and monocytes plays an important role in the MHC class II-restricted responses of specific T lymphocytes. It also serves as the major receptor of human immunodeficiency viruses (HIV).

CD45 is a trans-membrane protein tyrosine phosphatase (also called Leukocyte Common Antigen) that is expressed on all hematopoietic cells. Expression is at a higher density on lymphocytes whilst the expression is lower on other leukocytes like granulocytes and monocytes. In addition to the blood, bone marrow and lymphatics, since CD45 is found throughout the hematopoietic lineage, CD45 will be found wherever such cells constitute a significant portion of the tissue, e.g. spleen, thymus, and bone marrow.

Lymphocytes are defined by flow cytometry either through dual light scatter parameters, or alternatively (now considered the only recommended method in new guidelines) by the use of dual bright CD45 expression with side scatter properties. The lymphocyte population is used as the common denominator or reference point between the hematology and flow cytometry machines in order to calculate a CD4 T cell of total lymphocytes.

The absolute CD4 count is calculated by multiplying the CD4% (which can alternatively be defined as CD3+/CD4+ T cells) of the total lymphoid population defined by flow cytometry by the ALC, which is then expressed as number of cells per microlitre, or number of cells×106/t, or the number of cells×109/t.

Inter-laboratory variation ranging between 15-44% is, however, described for the widely used dual platform method (greater than 60% of returns in a recent U. K. NEQAS Immunology shipment have been reported). Theoretically, in order that all laboratories measure lymphocytes equally, the U. K. NEQAS, CDC, NCCLS, and others have devised very specific guidelines (1) for use of a "Lymphosum". The "Lymphosum" itself is a method of identifying the total lymphoid population by flow cytometry including all T cells (CD3+), all B cells (CD19+) and all Natural Killer cells (CD16+/56+), so that the sum of the individual components equals approximately 100% of lymphocytes.

Various gating strategies that include identification of bright CD45 positive cells (lymphocytes) have been recommended to ensure purity of the lymphoid population (2) and improve the quality of the assay, but this is not widely practiced in many countries. The practice of abbreviated panels, including only CD3/CD4 and CD8 is based loosely on international guidelines. It is practiced largely due to cost containment, and has limited quality control, especially on samples which are older than 6-24 hours, when cell disintegration results in poor cellular definition and hence problems occur with accurate identification and subsequent gating of lymphocytes. Use of CD3, CD4 and CD8 antibodies in a single tube to determine the percentage of CD4 positive T cells is therefore not recommended for use (1) as there is no means in the abbreviated panel of CD3, CD4 and CD8 only to validate the purity or completeness of the lymphocyte gate.

From the hematology analyzer perspective, white blood cell counts and especially automated differential counts should ideally be performed within 6 hours of venesection and preferably within 24 hours. There is currently no known hematology analyzer manufactured that reliably facilitates white cell and/or white blood cell differential counting after 36 hours after blood collection.

Further, different hematology analyzers use different methods of identifying lymphocytes and show variation in ALC reporting according to the specifications of the analyzer, even on fresh samples less than 6 hours old. Although the guidelines for identifying lymphocytes by flow cytometry are relatively clear, to date no recommended or universal method of identifying lymphocytes or other different types of white blood cell on a hematology analyzer exists, despite there being existing knowledge of very specific differential expression of CD45 on lymphocytes. ALC white blood cell differential counts are therefore neither quality controlled nor standardized between laboratories and results are therefore unreliable and not directly comparable between laboratories. Because the CD4 count is calculated from the ALC in the dual platform system, it follows that the inaccuracies of the ALC are translated to the CD4 count. Thus, the error in each independent step of each the separate systems in the dual platform method is multiplied at each subsequent step in the calculation.

In spite of the relatively wide inter-laboratory variation of CD4 result reporting, the dual platform flow cytometry system remains the most widely used and preferred system for CD4 testing. One of the main problems of the dual platform method lies in the identification of lymphocytes as the common denominator or reference point between the two platforms. An Absolute Lymphocyte Count (ALC) is a highly variable parameter between laboratories. Currently, although white blood cell (WBC) counts are well quality controlled, both internally on the instruments themselves and externally on various quality assessment schemes, white blood cell differential counting methods and techniques of identifying lymphocytes on various hematology analyzers are neither quality controlled or standardized. As ALCs are currently used as the common denominator and mainstay of dual platform system CD4 counting, it therefore follows that the documented variability of ALC reporting is carried over into CD4+ T cell result reporting.

Single Platform Testing

The single platform method (SP) of measuring CD4+ T cells uses flow cytometry only, and both the cell counting and the identification of the CD4+ T cells are performed on the same instrument, a flow cytometer. It is recommended due to the improved reproducibility of laboratory results, the inter-laboratory variation having been reported as varying between 10-18%.

There are several options for performing single platform CD4 testing. One option includes the use of a flow cytometer with a volumetric precision counting facility, e.g. the Ortho CytoronAbsolute (Ortho Diagnostic Systems, USA) but this instrument is no longer manufactured. The second option utilizes beads as a reference standard from which the cells themselves can be counted. The beads are added to the sample in a known concentration, either during manufacture or during sample preparation, in a specified volume, to a similar volume of blood and counted alongside the cells of interest on a flow cytometer. Bead-based counting, although less variable between laboratories, is, however, more technically intensive and relies heavily on accurate, precise pipetting, and also on the technical skills of the operator. Duplication of testing is also recommended to assess pipetting error and ensure accuracy of counting. This increases further the costs of bead-based testing.

Simplified, smaller single platform flow cytometers dedicated to CD4 enumeration (FACSCount, BDS, San Jose; Calif., USA) are also widely used. Although these instruments are considerably cheaper than flow cytometers, reagents costs for these instruments are more costly than for ordinary flow cytometry, thereby also prohibiting their use in many laboratories.

An additional problem of both the single platform and dual platform systems is that of the increased costs associated with "Lymphosum" testing. Unfortunately the obviously less expensive "CD4 only" alternatives do not offer sufficient built-in quality control to ensure accuracy and precision of individual sample testing.

Alternative Technologies for CD4+ T Cell Determination

There are also several alternative non-flow cytometric technologies for CD4+ T cell counting available. These include the Dynabead™ assay, Coulter Cytospheres Assay TRAX assay (and Microvolume Fluorimetry The Absolute Lymphocyte Count (ALC) has also been proposed as an alternative to CD4 enumeration where an ALC of less than 1000 cells/µl is used a substitute for a CD4+ T cell count of 200/µl or less. Poor correlation of these parameters, however, has been shown, and it has been suggested that an ALC substitute does not offer meaningful information for individual patient management.

The current dual methods of CD4 testing are therefore impractical and/or expensive, and do not provide results which are sufficiently accurate. A need thus exists to provide a method which is simple to perform, accommodates existing technologies and is more accurate than currently methods employed.

SUMMARY OF THE INVENTION

According to a first embodiment of the invention, there is provided a method of enumerating the number of cells of a cell type in a cell sample, the method comprising the steps of:

counting the white blood cells in the cell sample to obtain the white blood cell population of the sample;

determining the proportion or percentage of the cells of the cell type in the white blood cell population in the sample; and calculating the number of cells of the cell type in the sample.

The number of cells of the cell type in the sample may be calculated by relating the proportion or percentage of the cells of the cell type to the white blood cell population in the sample.

The cell type may be a lymphocyte sub-set, and in particular, a lymphocyte sub-set selected from the group comprising CD4+ lymphocytes, CD 45 cells, CD19 cells, CD16 and CD56 positive cells, CD8 cells, CD3 cells or any combination thereof. More particularly, the lymphocyte sub-set may be CD4+ lymphocytes. The CD4+ lymphocytes may be CD4+ T cells.

The sample may be whole unlysed blood, unfractionated, fractionated or lysed whole blood. Alternatively, the sample may be whole unlysed bone marrow, unfractionated, fractionated or lysed whole bone marrow.

Counting the white blood cells (CD45 positive leukocytes) in the sample will naturally involve identifying the white blood cells in the sample, and any suitable known, conventional or established method may be used for such counting (and identification), using any suitable hematology analyzer or flow cytometer. For example, identification of nuclear nucleic acid (DNA) staining may be employed as a method of counting the white blood cell population (i.e. the white cell count) in the sample. The white blood cell population in the sample may be defined by flow cytometry, either immunophenotypically as CD45+ cells, or, using a technique substantially similar to DNA staining, as nucleated cells. The white cell population may be counted directly using total CD45 expression to obtain a total white cell count, when incorporating beads as a single platform reference standard in the sample or using a volumetric precision counter.

Actual calculating of the number of CD4+ T cells in the sample may be performed by multiplying the white blood cell population in the sample by a factor, which is the proportion of CD4+ T cells in the white blood cell population when the proportion of CD4+ T cells of the white blood cell population is expressed as a fraction. If the proportion of CD4+ T cells in the white blood cell population is expressed as a percentage, then the white blood cell population will be multiplied by a factor which is a hundredth of the percentage ($\% \times 10^{-2}$).

The invention thus provides a dual-platform method of establishing (but not limited to) the number of CD4+ T cells in the sample, using two separate parameters.

Counting the white blood cells in the sample may, as indicated above, be by means of a suitable hematology analyzer. Any suitable hematology analyzer may be employed, examples being those available under the trade names GenS™, CELL-DYN™ 4000, and XE2100™, manufactured respectively by Beckman Coulter, Inc. (GenS™), Abbott (CELL-DYN™ 4000) and Sysmex Corporation (XE2100™). In turn, determining the proportion of CD4+ T cells in the white blood cells in the sample may, as indicated above, be by means of a suitable flow cytometer. Any suitable flow cytometer may be employed, examples being those available under the trade names EPICS™ XL and FACSCalibur™, manufactured respectively by Beckman Coulter, Inc. (EPICS™ XL) and BD Biosciences (FACSCalibur™).

While any suitable technique for counting the white blood cells in the sample may be employed, counting said white blood cells may, for example, be by a size discrimination technique, by an impedance measuring technique, or precision volumetric counting.

Similarly, while any suitable technique for determining the proportion of CD4+ T cells in the white blood cells in a sample may be employed, determining the proportion of CD4+ T cells in the white blood cells in the sample may, for example, be by means of flow-cytometric 90°/side scatter with CD4 expression. While the counting of the white blood cells and the determining of the proportion of CD4+ T cells in the sample may be carried out on separate instruments, namely a hematology analyzer and a flow cytometer, it may be possible to combine the functions of such instruments so that both the white blood cell count and the determination of the proportion or percentage of CD4+ T cells of the white blood cells can conveniently be carried out on a single or common instrument.

In a particular embodiment of the invention a dual-platform (i.e. double- or twin-platform) method may be employed, involving two separate instruments to obtain the CD4+ T cell population (i.e. the absolute CD4+ T cell count) in the sample, namely a hematology analyzer to obtain the white cell count and a flow cytometer to obtain the fraction or percentage of CD4+ T cells. The white cell count obtained from the hematology analyzer is then multiplied by the CD4+ T cell fraction or percentage (as indicated above), measured as a fraction of the population of white blood cells (defined as the CD45+ (positive-expressing cells) obtained from the flow cytometer. This calculation facilitates the generation of the absolute CD4+ T cell count.

Thus, for example, a Beckman Coulter GenS™ hematology analyzer may be used to obtain a white cell count on a blood sample, followed by measurement of the CD4+ T cell fraction or percentage of the white blood cell population (defined by the CD45+ expression thereof) using a Beckman Coulter EPICS™ XL flow cytometer, on the same blood sample.

Instead, a single-platform method may be employed, involving a single instrument, the total white cell count and the CD45+ T cell fraction or percentage of the total white cell population being obtained on a single instrument (which may be either a flow cytometer or a hematology analyzer). This may be effected by counting the white blood cells directly on a hematology analyzer having a facility for fluorescence measurement which can be altered to effect measurement of the fraction or proportion of CD45+ T cells of the total white cell population. Alternatively, the CD45+ T cell fraction or percentage of the total white cell population may be measured directly on a flow cytometer for a blood sample, which flow cytometer has had a suitable (commercially available) bead counting preparation (such as Beckman Coulter Flow-Count™ Fluorospheres) added thereto, the beads being counted simultaneously and being used as a standard from which the absolute number of CD45+ T cells can be calculated.

The method may additionally comprise one or more of the following steps:

calculating the number of lymphocytes in the sample by relating the proportion or percentage of high density CD45++ bright cells and low side scatter cells, a component of which is CD4 positive lymphocytes, to the white blood cell population in the sample, thereby to establish the population of lymphocytes in the sample;

calculating the number of monocytes in the sample by relating the proportion or percentage of moderate density CD45++ cells and medium side scatter cells, and dim moderate density CD4 cells, to the white blood cell population in the sample, thereby to establish the population of monocytes in the sample; and calculating the number of granulocytes in the sample by relating the proportion or percentage of dim low density CD45+ cells and CD4 negative cells and high side scatter cells to the white blood cell population in the sample, thereby to establish the population of granulocytes in the sample.

CD45 and CD4 may be combined either for use with a dual or a single platform system to provide at least a three-part (3-part) or at best, a five-part (5-part) white blood cell differential including the identification of granulocytes, monocytes, lymphocytes, basophils and eosinophils, in addition to the identification of CD4+ lymphocytes (T cells). Both percentages and absolute counts of each of the individual latter mentioned cellular compartments can be generated, as described above. This may be effected by counting the white blood cell compartments directly on a hematology analyzer having a facility for fluorescence measurement which can be altered to effect measurement of the fraction or proportion of relevant cells of the total white cell population e.g. granulocytes, and the like. Alternatively, the particular cell fraction or percentage of the total white cell population may be measured directly on a flow cytometer for a blood sample, which flow cytometer has had a suitable (commercially available) bead counting preparation (such as Beckman Coulter Flow-Count™ Fluorospheres) added thereto, the beads being counted simultaneously and being used as a standard from which the absolute number of the component cells e.g. granulocytes and the like can be calculated.

According to a second embodiment of the invention, there is provided a kit for use in enumerating the number of CD45+ T cells in a sample according to the method described above, the kit including antibodies for use in the method and instructions for performing the method. The kit may include software for analysis of flow cytometry or hematology analyzer data.

The antibodies may be CD4 and/or CD45 antibodies.

The kit may also include computer software for at least partially performing the method of cell enumeration described above.

According to a further embodiment of the invention, there is provided a machine readable medium comprising instructions, which when executed by a machine, cause the machine to perform, at least partially, the method steps substantially as described above. The machine readable medium may be configured for use in conjunction with a flow cytometer and/or a hematology analyzer, and may include instructions for analysis of flow cytometry data.

According to yet a further embodiment of the invention, there is provided a method of monitoring the immune status of a patient with HIV or other immune deficiency condition or disease, the method including the step of enumerating the number of CD45+ lymphocytes or CD45+ T cells in a cell sample from the patient by a method substantially as described above. In particular, the method may be used to determine or monitor the patient's response to antiretroviral treatment.

BRIEF DESCRIPTION OF THE FIGURES

FIG. 1 shows histograms of dual platform total white blood cell (CD45) assisted CD4 T cell enumeration:

FIG. 2 shows histograms of single platform total white blood cell (CD45) assisted CD4 T cell enumeration:

FIG. 3 shows histograms of a 6-part white blood cell differential including CD4+ lymphocytes based on use of CD45 and CD4:

DETAILED DESCRIPTION OF SOME EMBODIMENTS OF THE INVENTION

The invention will now be described, by way of non-limiting illustration, with reference to the following explanatory examples, with reference to the accompanying drawings.

Example 1

Dual-platform Method

A full blood sample was collected from a consenting adult in ethylene diamine tetra-acetic acid ($K_3$EDTA). This sample was delivered to the laboratory within 6 hours of venesection. Upon receipt in the laboratory the sample was subjected to a white blood cell count performed on a Beckman Coulter GenS™ hematology analyzer. A white cell count of $4.80 \times 10^9$/l was obtained.

Appropriate external quality assessment and internal quality control as recommended by the supplier was performed daily on this instrument to ensure that the white cell count was accurate and precise.

After the white blood cell count was obtained, blood taken from the same sample was prepared for flow cytometric analysis. Flow cytometric preparation involved dispensing a well-mixed 100 µl aliquot of whole blood into the bottom of a 12×75 mm test tube. Anti-CD4 phycoerthryrin (PE) monoclonal antibodies and CD45 Fluorescein-isothiocyanate (FITC) monoclonal antibodies were added (both obtained from Immunotech, Beckman Coulter, Inc., Miami, Fla.) according to the supplier's recommendations and incubated for 10 minutes at room temperature, in the dark.

The tube containing the 100 µl of blood with the added CD45 and CD4 antibodies was then prepared for flow cytometric analysis on a Beckman Coulter Q-Prep/Immuno-Prep™ Reagent System and Workstation, as directed by the supplier. This preparative step included adding a red blood cell lysing agent, a stabilizer and a fixative. The sample was then analyzed on a Beckman Coulter EPICS™ XL flow cytometer as set forth hereunder. Appropriate internal quality control including proper alignment and standardization for light scatter and fluorescence intensity, as well as color compensation, as recommended by the supplier was performed daily on this instrument to ensure that the flow cytometry results were accurate and precise.

Figure 1A:
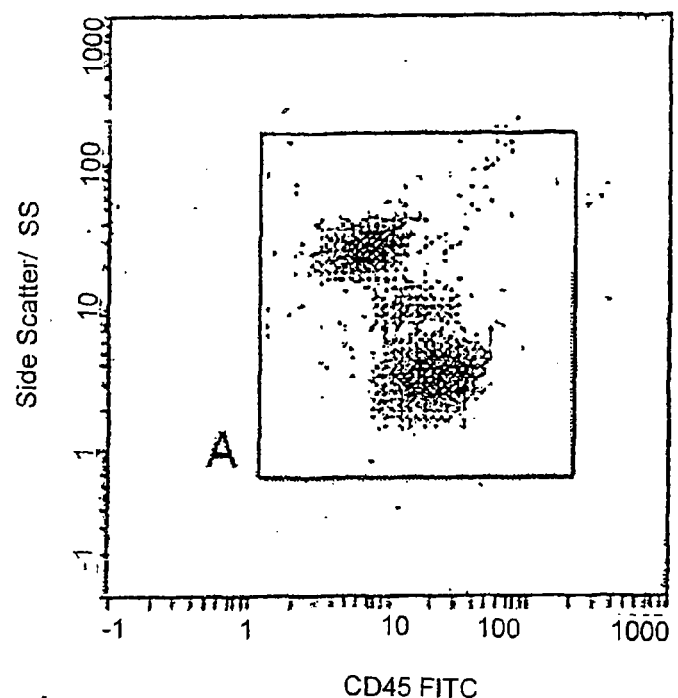
FIG. 1a shows a histogram of capture of total CD45 positive events (all white blood cells)
Figure 1B:
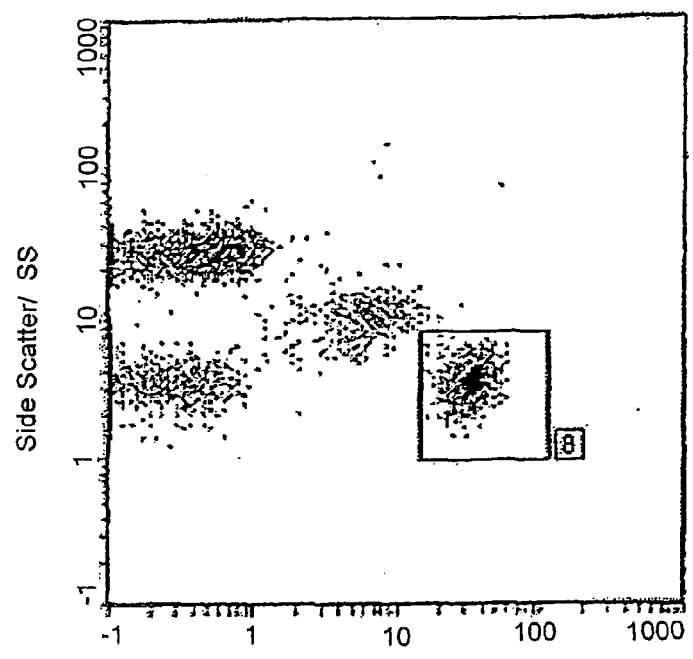
FIG. 1b shows a histogram of gated CD45 positive events with identification of CD4 positive lymphocytes.

Thus total leukocytes were first identified on a [CD45 FITC vs. side scatter (SS)] display (Region A in FIG. 1a). All CD45 positive gated events in Region A (the total number/population of leukocytes) were then displayed in FIG. 1b, containing only the CD45 positive cells, using a [CD4 PE vs. SS] display where CD4++ (high density) low side scatter lymphoid cells, were identified (Region B in FIG. 1b). A CD45+ lymphocyte (T cell) percentage of 16.5% was noted.

The absolute CD45+ lymphocyte (T cell) count was obtained by multiplying the white cell count obtained from the hematology analyzer by the CD45+ T cell fraction obtained by flow cytometry, i.e. $4.8 \times 10^9$/l multiplied by 16.5% divided by 100. This gave $0.792 \times 10^9$ CD45+ lymphocytes (T cells)/l (or 792 CD45+ lymphocytes (T cells)/µl).

In this method, the total leukocytes served as a common denominator or reference point for the dual-platform absolute CD45+ T cell counting, instead of using the lymphoid population as the common denominator or reference point, which is the existing state of the art for the dual platform methodology.

The gating strategy employed also made possible the calculation of the CD4+ T cell percentage of total lymphocytes, i.e. the number of events in Gate B (FIG. 1b) divided by the number of events in Gate C (FIG. 1a). Thus, 752 CD45+ events noted in Gate B were divided by 1416 CD45+ bright events noted in Gate C (FIG. 1a), i.e. 752/1416 (0.531 or 53.1%). This CD4 cell percentage of total lymphocytes, irrelevant to the present invention, was nevertheless available in case it was clinically relevant, e.g. in pediatric cases.

Figure 3A:
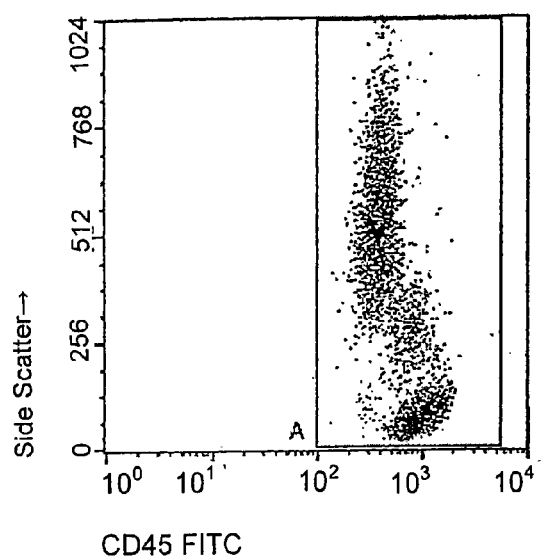
FIG. 3a shows a histogram of capture of total CD45 positive events (all white blood cells) (A)
Figure 3B:
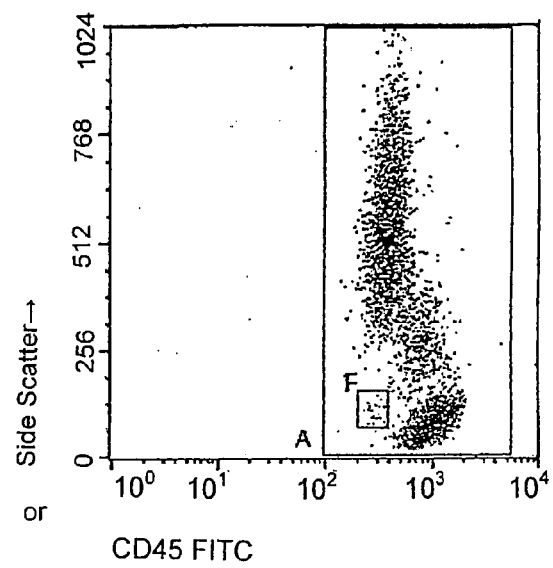
FIG. 3b shows the histogram of FIG. 3a including basophils (F)
Figure 3C:
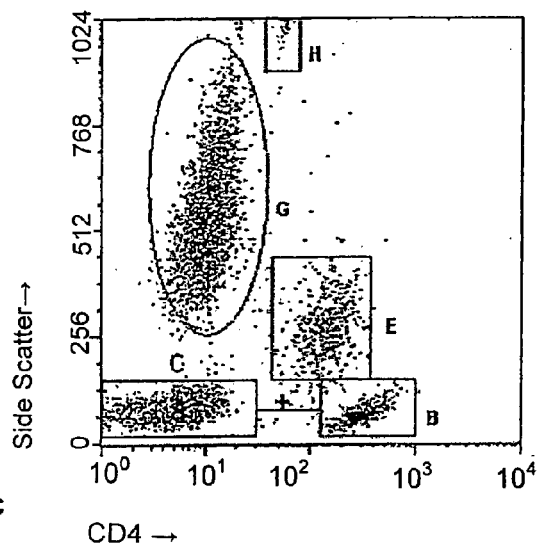
FIG. 3c shows a histogram of gated CD45 positive events with identification of CD4 positive lymphocytes (B), total lymphocytes (B+C−F, from histogram 3a), monocytes (E), granulocytes (G), eosinophils (H) and CD4+ lymphocytes (B).

The gating strategy employed also made possible the calculation of each of the individual components of the full white blood cell differential of this sample. In this analysis, total leukocytes were first identified on a [CD45 FITC vs. side scatter (SS)] display (Region A in FIG. 3a). All CD45 positive gated cells (i.e. gated events) in Region A (the total number of leukocytes) were then displayed in FIG. 3b containing only the CD45 positive cells, using a [CD4 PE vs. SS] display. These displays included lymphocytes (FIGS. 3a and 3b, Gate C), monocytes (FIGS. 3a and 3b, Gate E), basophils (FIG. 3a, Gate F), granulocytes (FIGS. 3a and 3b, Gate G), and eosinophils (FIG. 3b, Gate H).

The number of events in each of these respective gates (i.e. the number of events in Gate C (FIGS. 3a and 3b), Gate E (FIGS. 3a and 3b), Gate F (FIG. 3b) and Gate G (FIGS. 3a and 3b) and Gate H (FIG. 3b), divided by the number of events in Gate A (FIG. 3a) were thus used to generate the respective percentages of the individual white blood cell differential components.

Thus, the following calculations were possible:

Lymphocyte percentage:

1416 high density CD45 brightly positive events with low side scatter, and of which a component could be CD4 positive, noted in Gate C (FIG. 3a), were divided by 4750 CD45 positive events noted in Gate A (FIG. 3a), i.e. 1416/4750 (0.298 or 29.8%).

Monocyte percentage:
380 moderate density CD45 moderately bright positive events with moderate side scatter and moderate density CD4 expression or positivity, noted in Gate E (FIGS. 3a and 3b), were divided by 4750 CD45 positive events noted in Gate A (FIG. 3a), i.e. 380/4750 (0.080 or 8.0%).

Basophil percentage:
51 low density CD45 dimly positive events with low side scatter, and negative CD4, in noted Gate F (FIG. 3a), were divided by 4750 CD45 positive events noted in Gate A (FIG. 3a), i.e. 51/4750 (0.010 or 1.0%).

Granulocyte percentage:
2758 low density CD45 dimly positive events with high side scatter (and negative CD4 expression) noted in Gate G (FIGS. 3a and 3b), were divided by 4750 CD45 positive events noted in Gate A (FIG. 3a), i.e. 2759/4750 (0.581 or 58.1%).

Eosinophil percentage:
145 moderate density CD45 moderately bright positive events with very high side scatter and some weak autofluorescence noted on FL2, noted in Gate H were divided by 4750 CD45 positive events noted in Gate A (FIG. 3a), i.e. 144/4750 (0.031 or 3.1%).

The absolute counts of each of the components of the white blood cell differential including Gates C, E, F, G and H was obtained by multiplying the white cell count obtained from the hematology analyzer by the respective white blood cell differential fraction obtained by flow cytometry.

Thus, the following absolute calculations were possible:
Absolute lymphocyte count
$4.8 \times 10^9$/l multiplied by 29.8% (FIG. 3a, Gate C) divided by 100. This gave $1.430 \times 10^9$ lymphocytes/l (or 1430 lymphocytes/µl)

Absolute monocyte count
$4.8 \times 10^9$/l multiplied by 8.0% (FIGS. 3a and 3b, Gate E) divided by 100. This gave $0.384 \times 10^9$ monocytes/l (or 384 monocytes/µl).

Absolute basophil count
$4.8 \times 10^9$/l multiplied by 1.0% (FIG. 3a, Gate F) divided by 100. This gave $0.048 \times 10^9$ basophils/l (or 48 basophils/µl)

Absolute eosinophil count
$4.8 \times 10^9$/l multiplied by 3.1% (FIG. 3b, Gate H) divided by 100. This gave $0.149 \times 10^9$ eosinophils/l (or 149 eosinophils/µl).

Absolute granulocyte count
$4.8 \times 10^9$/l multiplied by 58.1% (FIGS. 3a and 3b, Gate G) divided by 100. This gave $2.789 \times 10^9$ granulocytes/l (or 2789 granulocytes/µl).

Example 2

Single-platform Method

A full blood sample was collected in $K_3$EDTA from a consenting adult patient. This sample was delivered to the laboratory within 6 hours of venesection. Upon arrival in the laboratory the sample was prepared for flow cytometric analysis. Flow cytometric preparation involved dispensing (by reverse pipetting) a well-mixed 100 µl aliquot of the sample (whole blood) into the bottom of a 12×75 mm test tube.

Anti-CD4 PE monoclonal antibodies and CD45 FITC monoclonal antibodies were added (both obtained from Immunotech, Beckman Coulter, Inc., Miami, Fla.) according to the supplier's recommendations and incubated for 10 minutes at room temperature, in the dark. The tube containing the 100 µl of blood with the added CD45 and CD4 antibodies was then prepared for flow cytometric analysis using the above mentioned Q-Prep/ImmunoPrep™ Reagent System and Workstation, as directed by the supplier.

After this whole blood preparation step, which included adding a red cell lysing agent, a stabilizer and a fixative, commercially available bead reagents (Flow-Count™ Fluorospheres obtained from Beckman Coulter, Inc., Miami, Fla.) were added to the sample as directed by the supplier. This Fluorosphere addition step involved using a very well mixed 100 µl aliquot of the Flow-Check™ Fluorospheres. The assayed concentration of the Fluorospheres was stated to be 1000 µl. The Fluorospheres were added by a reverse pipetting technique with careful attention not to pipette air bubbles. Good reverse pipetting technique was crucial to the accuracy and precision of these test results. The sample was analyzed within 2 hours of the addition of the Fluorospheres and was well mixed prior to flow-cytometric analysis.

Figure 2A:
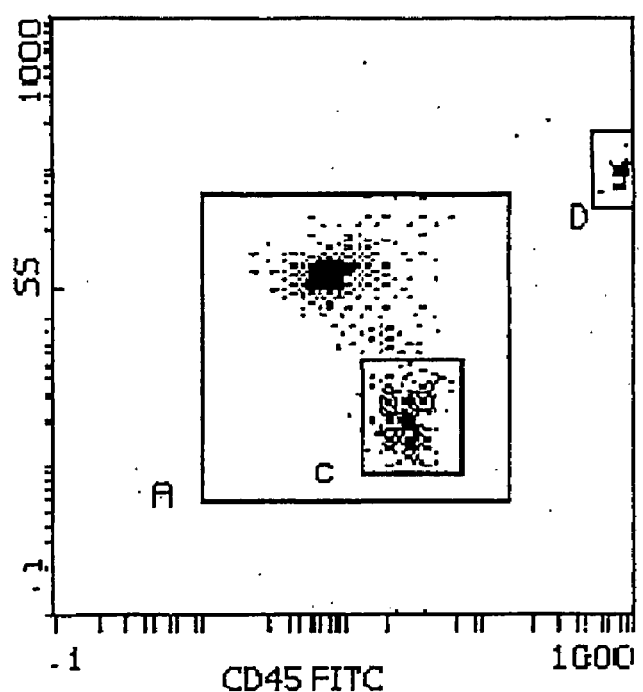
FIG. 2a shows a histogram of capture of total CD45 positive events (all white blood cells), excluding fluorospheres.
Figure 2B:
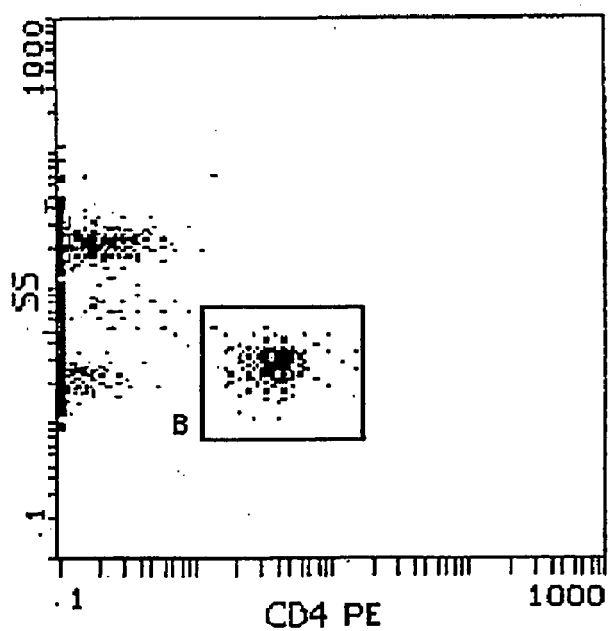
FIG. 2b shows a histogram of gated CD45 positive events with identification of CD4 positive lymphocytes.
Figure 2C:
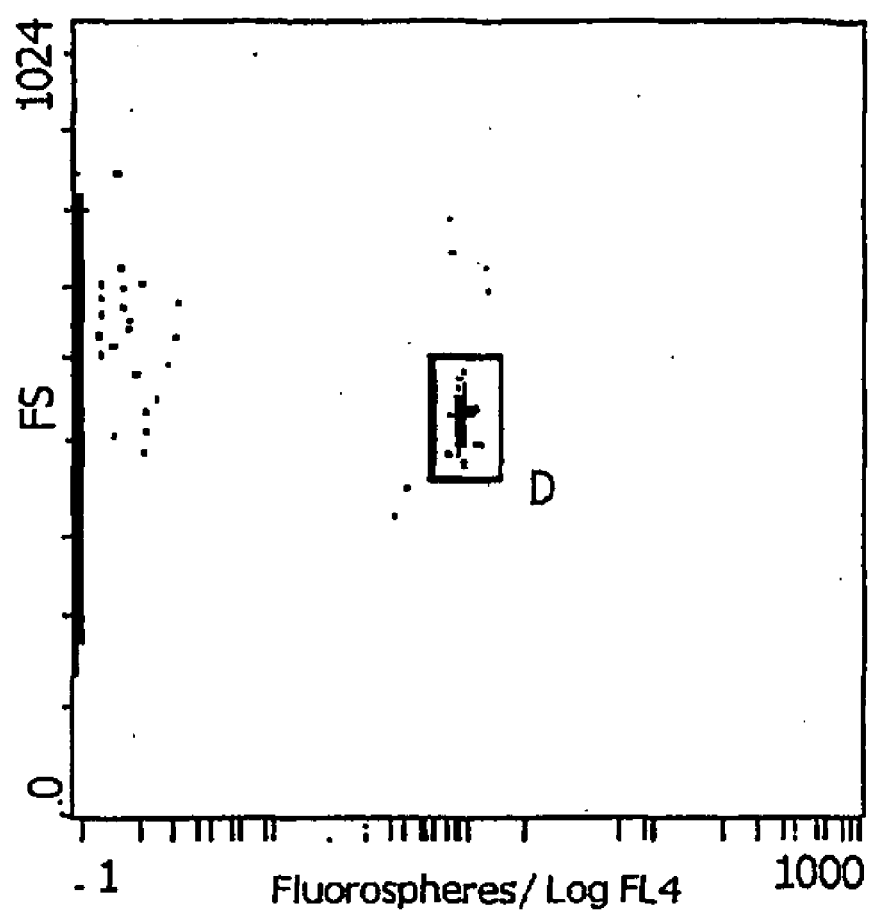
FIG. 2c shows a histogram of capture of total CD45 positive events (all white blood cells).

The sample was then analyzed on a Beckman Coulter EPICS™ XL flow cytometer until 1000 Fluorospheres were counted. Appropriate internal quality control including proper alignment and standardization for light scatter and fluorescence intensity as well as color compensation, as recommended by the supplier was performed daily on this instrument to ensure that flow cytometry results were accurate. In this analysis, total leukocytes were first identified on a [CD45 FITC vs. side scatter (SS)] display (Region A in FIG. 2a). All CD45 positive gated cells (i.e. gated events) in Region A (the total number of leukocytes) were then displayed in FIG. 2b containing only the CD45 positive cells, using a [CD4 PE vs. SS] display where CD4++, low side scatter lymphoid cells were identified (Region B in FIG. 2b). The Fluorosphere population was shown in a separate histogram of [Forward Scatter (abbreviated as FS) vs Fluorospheres] the latter of which were detected on log scale of FL4 (fluorescence detector number 4) (Region D, FIG. 2c).

The absolute CD45 positive cell count (total white blood cell count) was calculated as directed by the Fluorosphere manufacturer's instructions (Beckman Coulter Flow-Count™), i.e. total number of cells counted divided by the total number of Fluorospheres counted, and then multiplied by the Flow-Count™ Fluorosphere assayed concentration, gave the absolute count/µl.

The CD45 positive leukocyte count was therefore calculated as follows:

The Region A count of 4737 (total CD45 positive cells counted) was divided by the Region D count of 1000 (total Fluorospheres counted), and then multiplied by 1000/µl (the Fluorosphere assayed concentration), which gave a white cell count of 4737/µl or $4.737 \times 10^9$/l (the absolute CD45 positive leukocyte or white cell count). The absolute CD45+ T cell count was obtained by multiplying this calculated CD45 positive white cell count by the percentage of CD4++ low side-scatter lymphocytes (T cells) counted within the CD45 positive+leukocyte population (Region B, FIG. 2b i.e. 4737/µl multiplied by 16.2% (i.e. by 0.162). This gave 766 CD4 lymphocytes (T cells)/µl (or $0.766 \times 10^9$ CD45+ lymphocytes (T cells)/l).

In this method, the total CD45+ positive leukocyte count served as the base line for the absolute CD45+ T cell counting instead of using the total lymphoid population (defined by light scatter or by CD45 bright or CD3 positive lymphocyte count as the base line, which is the single platform methodology.

Alternatively, the CD4 lymphocyte (T cell) count can be directly calculated. This is achieved by taking the number of events in FIG. 2b, Region B (766) and dividing this number by the FIG. 2c, Region D count (1000-total Fluorospheres counted), and then multiplying by 1000/µl (the Fluorosphere assayed concentration), which gave 766 CD4 lymphocytes (T cells)/µl or $0.766 \times 10^9$ CD45+ lymphocytes (T cells)/l, which is equivalent to the absolute CD45+ T cell count).

The gating strategy employed also made possible the calculation of the CD4+ T cell percentage of total lymphocytes, i.e. the number of cells in Gate B (Figure (IV)) divided by the number of cells in Gate C (Figure III). Thus, 766 events noted in Gate B were divided by 1421 CD45++ bright events noted in Gate C, i.e. 766 divided by 1421 (0.539 or 53.9%). This value was not, however, used in the generation of the CD45+ count, and was merely extra information available in case the CD4 percentage of lymphocytes was clinically relevant, e.g. in pediatric cases.

In a similar fashion to the dual platform method, this single platform methodology can be used to calculate the respective percentages and absolute counts for a 5-part white blood cell differential on this sample. The method is identical to that described for the dual platform technology except that beads or an appropriate single platform technology including volumetric Ortho Cytoron™ counting is used as the directing counting mechanism and is applicable to whole or lysed blood samples.

Advantages of the invention, particularly as described with reference to the above examples, are that the use of a count of the white blood cell population incorporating the use of CD45 expression as the basis for calculating the number of CD45+ T cells in cell samples facilitates accurate determinations after delays of up to several days after sample collection. Both CD45 and CD45+ T cell expressions are preserved with only minor losses of fluorescence intensity for greater than 120 hours, even after loss of forward scattering properties. Indeed, both the CD45+ leukocyte- and the side-scattering features of white blood cells promise to be retained for up to 7 days after sample collection. By virtue of including both the CD45+ leukocyte- and side-scattering parameters, technical errors can be avoided and irrelevant cellular events arising from, for example, monocytes (specifically related to absolute CD4 lymphocyte (T cell) counts) or red blood cells, can be excluded while relevant lymphoid cells, e.g. those with apoptotic scatter features, can be included.

Additional use of the invention with respect to the identification of the components of the white blood cell differential count and the enumeration thereof can significantly alter the present hematology analyzer state of the art. Given that there is adequate retention of both the CD45 and CD4 molecules several days after the time of venesection as described above and that the basis of measuring the cells is by CD45 and CD4, a total white blood cell count and full differential with absolute counts can be supplied several days after venesection as opposed to the 24 hour limit given by most hematology analyzer manufacturers. This feature adds a facility of delayed testing of several days and a new dimension which is not currently a feature of state of the art hematology analyzers. The method is therefore suitable for generating white cell counts with full 5-part differentials and absolute differential counts on samples which are already several days old.

The approach of the present invention is particularly amenable to pediatric samples where small quantities of blood are available. In the absence of CD45+ leukocyte staining, unlysed and nucleated red blood cells may drastically interfere with the definition of both CD45+ T lymphocyte absolute counts and CD45+ T lymphocyte fraction-or percentage values. In infants and children the CD45+ T lymphocyte percentage counts are used as the clinically relevant parameter because of the age-dependent variability of the CD45+ T absolute counts. Use of CD45+ leukocyte counts as a basis facilitates use of precise CD45+ T lymphocyte fraction-or percentage values by identifying the CD45++ T cells as a function the bright CD45++ leukocyte cells.

The main advantage of the CD45 assisted dual platform CD4 enumeration system is that it represents the only reliable quality controlled system for CD4 lymphocyte counting in a single test tube. Whereas single platform systems of counting including bead based or volumetric precision delivery systems have been reported as offering better accuracy, they rely on the duplication of the reading of at least one of the components of the duplication (i.e. CD3 duplicate) to reproduce and quality assess the absolute count (bead based counting, especially, is prone to error introduced by errors of pipetting). The DP CD45 assisted dual platform "PanLeucogating" CD4 enumeration system utilizes the white cell count which has the "built-in" quality control through quality control of the white cell count on the hematology analyzer itself, thus leading to the conclusion of good quality control in a single test tube. External isotype controls to assess non-specific binding of monoclonal antibody isotype are also not required in this system.

While the invention is relatively easy to perform, the applicant expects that the calculation of the CD45+ T cell enumeration or other white blood cell differential component populations as previously described, need not be performed manually, and a computer program for performing this calculation may be provided. The computer program may include computer executable instructions suitable for use on a flow cytometer and/or hematology analyzer.

A kit may also be provided to enable a user to perform the invention, the kit including one or more antibodies and instructions for performing the invention. The antibodies would typically be CD4 and/or CD45 antibodies. The kit may also include the computer program, or include instructions for use in conjunction with the program.

The method of the present invention specifically for CD4 lymphocyte enumeration avoids the need for Lymphocyte referencing, is relatively robust, reproducible between laboratories and accurate, while being easy to use and comparatively inexpensive and easily implemented. The method is also suitable for use on samples which are already several days old.

REFERENCES

1. CDC-Centers for Disease Control and Prevention 1997 Revised guidelines for performing CD4+ T cell determinations in persons infected with human immunodeficiency virus (HIV). MMWR 1997; 46:1-29.
2. Schnizlein-Bick C, Mandy F, O'Gorman M, Paxton H, Nicholson J K A, Hultin L E, Gelman R S, Wilkening C and Livnat D. Use of CD45 gating in three and four color flow cytometric immunophenotyping: Guideline from the NIAID, Division of AIDS. Cytometry 2002, 50 (2); 46-52.
3. Glencross D K, Scoff L, Jani/. V., Barnett D and Janossy G. CD45 assisted PanLeucogating for Accurate, Cost Effective Dual Platform CD45+ T cell Enumeration. Cytometry Clinical Cytometry, 2002 Special Issue-CD4: 20 years and Counting: 50 (2); 69-77.

The invention claimed is:
1. A kit including antibodies, wherein the antibodies consist of anti-CD4 and anti-CD45 antibodies for use in enumerating the number of CD4+ cells in a sample and are conjugated to a label for detection with flow cytometry.

2. A kit according to claim 1, which further includes instructions for performing a method of enumerating the number of CD4+ cells in a cell sample.

3. A kit including antibodies, wherein the antibodies consist of anti-CD4 and anti-CD45 antibodies for use in enumerating the number of CD4+ cells in a sample and are conjugated to a label for detection with flow cytometry, which further includes one or more reagents selected from the group consisting of a red cell lysating agent, a stabilizer, a fixative, control cells, and bead reagents.

* * * * *